United States Patent [19]

Frank et al.

[11] 4,021,442
[45] May 3, 1977

[54] PRODUCTION OF 1-ALKYL-5-NITROIMIDAZOLES

[75] Inventors: Anton Frank; Helmut Karn, both of Ludwigshafen; Toni Dockner, Meckenheim, all of Germany

[73] Assignee: BASF Aktiengesellschaft, Ludwigshafen, Germany

[22] Filed: Mar. 11, 1975

[21] Appl. No.: 557,270

[30] Foreign Application Priority Data

Mar. 25, 1974  Germany .......................... 2414280

[52] U.S. Cl. .............................................. 260/309
[51] Int. Cl.² ...................................... C07D 233/92
[58] Field of Search .................................. 260/309

[56] References Cited

UNITED STATES PATENTS 3,487,087  12/1969  Sarett et al. ........................ 260/309
3,786,061  1/1974  Novello et al. ..................... 260/309

*Primary Examiner*—Natalie Trousof
*Attorney, Agent, or Firm*—Johnston, Keil, Thompson & Shurtleff

[57] ABSTRACT

1-Alkyl-5-nitroimidazoles are prepared by reacting a 5-nitroimidazole with an alkylating agent in the presence of an aliphatic carboxylic acid. The products are intermediates for the production of dyes, textiles auxiliaries and insecticides.

5 Claims, No Drawings

PRODUCTION OF 1-ALKYL-5-NITROIMIDAZOLES

This Application discloses and claims subject matter described in German Patent Application P 24 14 280.1, filed Mar. 25, 1974, which is incorporated herein by reference.

The invention relates to a process for the production of a 1-alkyl-5-nitroimidazole by the reaction of a 5-nitroimidazole with an alkylating agent in the presence of an aliphatic carboxylic acid.

It is known for Arzneimittelforschung, volume 16 (1966), pages 23 to 29, that the corresponding 1-methyl-5-nitroimidazole is formed from 5-nitroimidazole by reaction with dimethyl sulfate of diethyl sulfate in toluene, dimethylformamide or water as a solvent. This method is unsatisfactory on an industrial scale as regards yield, purity and ease of processing the end product.

It is an object of this invention to provide a new process for producing 1-alkyl-5-nitroimidazoles in a simpler and more economical manner and in better yields and purity.

We have found that a 1-alkyl-5-nitroimidazole of the formula (I):

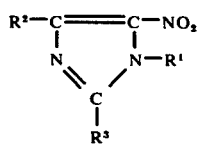

in which $R^1$ is alkyl and $R^2$ and $R^3$ are identical or different and each is hydrogen or an aliphatic, araliphatic, cycloaliphatic or aromatic radical is obtained in an advantageous manner by the reaction of a nitroimidazole with an alkyl ester by reacting a 5-nitroimidazole of the formula (II)

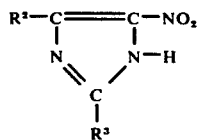

in which $R^2$ and $R^3$ have the above meanings, with an alkylating agent of the formula (III):

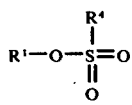

in which $R^4$ is an aromatic radical or the radical $-O-R^1$ and $R^1$ has the above meaning, in the presence of an aliphatic carboxylic acid.

When 2-methyl-5-nitroimidazole and dimethyl sulfate are used the reaction may be represented by the following equation:

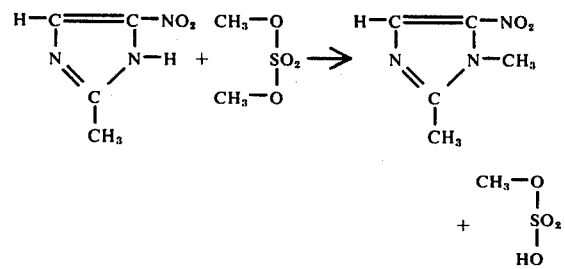

The process according to the invention gives a 1-alkyl-5-nitroimidazole in a simpler and more economical manner and in better yield and purity than the known methods. Troublesome and expensive purification treatments are dispensed with and the isolation of the end product is quicker and more reliable even on an industrial scale. All these advantageous results are surprising having regard to the prior art.

5-nitroimidazoles of the formula (II) which bear a replaceable hydrogen atom on a nitrogen atom are used as starting materials. The substituent in the 5-position in the molecule may also be present in the 4-position because of tautomerism.

Preferred starting materials (II) and (III) and consequently preferred end products (I) are those in whose formulae $R^2$ and $R^3$ are identical or different and each is alkyl of one to 18 and preferably of one to eight carbon atoms, cycloalkyl of five or six carbon atoms, aralkyl of seven to 12 carbon atoms or phenyl, $R^1$ is alkyl of one to four carbon atoms and $R^4$ is unsubstituted or substituted phenyl or tolyl or the radical $-O-R^1$ in which $R^1$ has the above meaning. The said radicals may bear groups which are inert under the reaction conditions, for example alkyl of one to four carbon atoms or nitro, as substituents.

For example in addition to 5-nitroimidazole itself the starting material (II) may be the following substituted imidazoles: 2-methyl-5-nitroimidazole, 2-ethyl-5-nitromidazole, 2-p-nitro-phenyl-5-nitroimidazole, 2-cyclohexyl-5-nitroimidazole, 2-isopropyl-5-nitroimidazole, 2-benzyl-5-nitroimidazole, 2-phenyl-5-nitroimidazole and corresponding imidazoles bearing a substituent in the 4-position;

2,4-dimethyl-5-nitroimidazole,
2-cyclopentyl-4-ethyl-5-nitroimidazole,
2-toluyl-4-phenyl-5-nitroimidazole,
4,5-diethyl-5-nitroimidazole,
2,4-dicyclohexyl-5-nitroimidazole,
2,4-dibenzyl-5-nitroimidazole and
2,4-diphenyl-5-nitroimidazole.

For example the following starting materials (III) may be used: diisobutyl, diisopropyl, dimethyl, dipropyl or diethyl sulfate; methyl, ethyl, isopropyl, isobutyl or propyl esters of benzene-sulfonic, toluenesulfonic, 2,5-dimethylbenzenesulfonic, 4-chlorobenzenesulfonic and 4-methoxybenzenesulfonic acids.

Starting material (II) is reacted with starting material (III) in a stoichiometric amount or in an excess and preferably in a molar ratio of from 1 to 2 moles of starting material (III) per mole of starting material (II). The reaction is carried out as a rule at a temperature of from 20° to 110° C and preferably from 60° to 80° C at atmospheric or superatmospheric pressure, continuously or batchwise. Preferred aliphatic carboxylic acids are alkanoic acids of one to six carbon atoms which may bear groups or atoms which are inert under the reaction conditions, for example chloro, alkyl of one to four carbon atoms or carbalkoxy of two to four carbon atoms as substituents. Equivalent amounts of polybasic acids may be used instead of monobasic acids.

For example the following acids are suitable: chloroacetic acid, dichloroacetic acid, trichloroacetic acid, oxalic acid, formic acid, cyanoacetic acid, acetic acid, propionic acid, butyric acid, isobutyric acid, glycolic acid, lactic acid, tartaric acid, citric acid, caprylic acid, trimethylacetic acid and β-chloropropionic acid, succinic acid, malonic acid and appropriate mixtures Formic acid and acetic acid are particularly preferred. The acids may be used in concentrated form, mixed with one another and/or with a solvent, particularly water. A pH of from 0 to 1 is advantageously set up in the reaction mixture. The acid is generally used in an amount of from 200 to 500% and preferably from 250 to 350% by weight based on the starting material (II).

The reaction may be carried out as follows: a mixture of starting materials (II) and (III) and acid is kept for from two to four hours at the reaction temperature while mixing well. Unreacted starting material (II) may be separated from the reaction mixture by a conventional method, for example by evaporation of solvent, addition of water, possibly neutralizing the acid, cooling and filtering, and returned to the reaction. The end product may be isolated from the filtrate by a conventional method, for example by adding ammonia or caustic alkali solution, cooling and filtration.

In an advantageous embodiment of the process according to the invention unreacted starting material (II) is conveniently separated by adjusting the acid reaction mixture with aqueous ammonia solution to a pH of from 1 to 3 and preferably 1.8, leaving the mixture for some time, for example half to 2 hours, at a low temperature, for example 0° to +12° C, separating the deposited unreacted starting material (II) and adjusting the filtrate to a pH of from 8 to 14 and preferably 10 with ammonia or caustic alkali solution, for example caustic soda solution. The end product (I) is isolated by filtration or by extraction and distillation of the extractant, for example ethyl acetate or ether.

The compounds which can be prepared according to the process of the invention are used in human and veterinary medicine against Protozoan diseases. Thus they may be used in controlling pathogens of sleeping sickness, of skin diseases, mucous membrane diseases, dourine, nagana, surra, hemoglobinemia and other animal diseases, and they are advantageous not only against flagellata but also against rhizopoda, ciliates and sporozoa, for example in the case of amoebic dysentery, malaria, bovine hemoglobinurea and cattle fever.

The compounds which can be prepared according to the process of the invention are moreover intermediates for the production of dyes, textile assistants and insecticides. They have chemotherapeutic properties in the therapy of colpitis. "Arzneimittelforschung", volume 16 (1966), pages 23 et seq. is referred to for details of applications.

The following Examples illustrate the invention. The parts specified in the Examples are by weight. They bear the same relation to parts by volume as the kilogram to the liter.

EXAMPLE 1

600 parts of formic acid (85%), 225 parts of 2-methyl-5-nitroimidazole and 250 parts of dimethyl sulfate are heated in a stirred vessel for 4 hours under reflux (80° C). The formic acid is then distilled off in vacuo. The residue which remains is dissolved in 400 parts of water, neutralized to pH 1.8 with aqueous ammonia solution and cooled to from 0° to +5° C. The unreacted 2-methyl-5-nitroimidazole is deposited and is centrifuged off. The mixture is then adjusted to pH 10 with aqueous ammonia solution and 1,2-dimethyl-5-nitroimidazole is separated at 10° C. 75 parts of 2-methyl-5-nitroimidazole and 145 parts of 1,2-dimethyl-5-nitroimidazole of the melting point 137° to 140° C are obtained. The yield based on reacted 2-methyl-5-nitroimidazole is 87% of theory.

EXAMPLE 2

202 parts of 5-nitroimidazole is dissolved in 600 parts of formic acid (90% by weight), 250 parts of dimethyl sulfate is added and the whole is heated for 6 hours. The formic acid is distilled off in vacuo. 420 parts of water is added to the residue, the whole cooled to from 0° to 5° C and the unreacted 5-nitroimidazole (60 parts) is centrifuged off. The mixture is adjusted to pH 10 with aqueous ammonia solution (25% by weight) and the precipitate is separated at 0° to 5° C. 130 parts of 1-methyl-5-nitroimidazole having a melting point of 58° to 60° C is obtained; this is equivalent to a yield of 82% of theory based on reacted 4(5)-nitroimidazole.

EXAMPLE 3

155 parts of 2-isopropyl-5-nitroimidazole, 350 parts of formic acid and 126 parts of dimethyl sulfate are heated under reflux for 2 hours. The formic acid is distilled off in vacuo and the residue which remains is dissolved in 500 parts of water. A pH of 1.8 is set up with dilute aqueous ammonia solution and the solution is cooled for 2 hours at +5° C. The unreacted 2-isopropyl-5-nitroimidazole (15 parts) is suction filtered and the filtrate is adjusted to pH 10 by adding aqueous ammonia solution. After cooling for 2 hours at 5° C the mixture is suction filtered and the end product is dried. 110 parts of 1-methyl-2-isopropyl-5-nitroimidazole having a melting point of 56° C is obtained and this is equivalent to a yield of 72% of theory based on reacted 2-isopropyl-5-nitroimidazole.

EXAMPLE 4

127 parts of 4-methyl-5-nitroimidazole is heated under reflux with 350 parts of forming acid and 126 parts of dimethyl sulfate for 4 hours. The formic acid is distilled off in vacuo and the residue is dissolved in 500 parts of water and adjusted to pH 1.8 with aqueous ammonia solution. The mixture is cooled to 5° C and the unreacted 4-methyl-5-nitroimidazole is suction filtered. The filtrate is adjusted to pH 10 with aqueous ammonia solution and is continuously exhaustively extracted with ethyl acetate. The extract is evaporated in vacuo. The oily residue crystallizes on standing. 47 parts of unreacted 4-methyl-5-nitroimidazole and 66 parts of 1,4-dimethyl-5-nitroimidazole melting at 45° C are obtained; this is equivalent to a yield of 74% of theory.

EXAMPLE 5

225 parts of 2-octyl-5-nitroimidazole is boiled under reflux with 500 parts of formic acid and 126 parts of dimethyl sulfate for 4 hours, the formic acid is distilled off in vacuo and 500 parts of water is added to the residue. The unreacted 2-octyl-5-nitroimidazole (72 parts) is separated and the aqueous phase is adjusted with aqueous ammonia solution to pH 10 so that the 1-methyl-2-octyl-5-nitroimidazole separates as an oily substance. The crude product is dissolved in ether and saturated with hydrogen chloride while cooling. 123 parts of 1-methyl-2-octyl-5-nitroimidazole having a melting point of 141° C is obtained and this is equivalent to a yield of 66% of theory based on the 2-octyl-5-nitroimidazole reacted.

EXAMPLE 6

127 parts of 2-methyl-5-nitroimidazole, 350 parts of acetic acid and 126 parts of dimethyl sulfate are boiled under reflux for 4 hours. The acetic acid is distilled off in vacuo and the residue is dissolved in 500 parts of water and adjusted to pH 1.8 with aqueous ammonia solution. After cooling to from 0° to 5° C the unreacted 2-methyl-5-nitroimidazole is suction filtered, the filtrate is adjusted to pH 10 and after cooling the 1,2-dimethyl-5-nitroimidazole is isolated. In addition to 30.4 parts of starting material (II) there is obtained 81 parts of 1,2-dimethyl-5-nitroimidazole (melting point 140° C); this is equivalent to a yield of 75.5% of theory.

We claim:

1. A process for the production of a 1-alkyl-5-nitroimidazole of the formula:

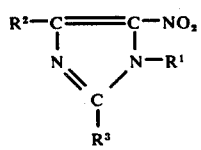

(I)

in which $R^1$ is an alkyl of 1 to 4 carbons and $R^2$ and $R^3$ are identical or different and each is hydrogen or an alkyl of one to 18 carbons, cycloalkyl of five or six carbons, aralkyl of seven to 12 carbons or phenyl, by the reaction of a nitroimidazole with an alkyl ester, wherein a 5-nitroimidazole of the formula:

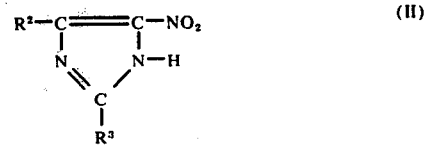

(II)

in which $R^2$ and $R^3$ have the above meanings is reacted in the presence of formic acid with an alkylating agent of the formula:

(III)

in which $R^4$ is phenyl or tolyl or the radical $-O-R^1$ and $R^1$ has the above meanings at a temperature of from 60° to 80° C.

2. A process as set forth in claim 1 wherein the reaction is carried out with from 1 to 2 moles of starting material (III) per mole of starting material (II).

3. A process as set forth in claim 1 wherein the reaction is carried out with the acid in an amount of from 200 to 500% by weight based on starting material (II).

4. A process as set forth in claim 1 wherein the acid reaction mixture is adjusted to pH from 1 to 3 with aqueous ammonia solution, the mixture is left for half an hour to 2 hours at 0° to +12° C, the deposited unreacted starting material (II) is separated, the filtrate is adjusted to pH from 8 to 14 with ammonia or a caustic alkali solution and the end product is isolated by a conventional method.

5. A process as set forth in claim 1 wherein $R^2$ and $R^3$ are identical or different and each is hydrogen or an alkyl of 1–8 carbon atoms.

* * * * *